(12) United States Patent
Hunter, Jr.

(10) Patent No.: US 8,356,601 B2
(45) Date of Patent: Jan. 22, 2013

(54) ARM STABILIZER DEVICE AND METHODS

(76) Inventor: Alton Lee Hunter, Jr., Columbia, TN (US)

( * ) Notice: Subject to any disclaimer, the term of this patent is extended or adjusted under 35 U.S.C. 154(b) by 13 days.

(21) Appl. No.: 13/087,841

(22) Filed: Apr. 15, 2011

(65) Prior Publication Data

US 2012/0103344 A1    May 3, 2012

Related U.S. Application Data

(63) Continuation-in-part of application No. 12/550,701, filed on Aug. 31, 2009, now Pat. No. 8,230,864.

(51) Int. Cl.
*A61G 15/00* (2006.01)
*A61F 5/37* (2006.01)
*A47D 11/00* (2006.01)

(52) U.S. Cl. ............ 128/845; 128/878; 5/647

(58) Field of Classification Search .......... 128/845–846, 128/869–870, 877–879; 602/5, 20–23, 32, 602/36; 5/623–624, 646–647, 650–651, 5/601

See application file for complete search history.

(56) References Cited

U.S. PATENT DOCUMENTS

| | | | |
|---|---|---|---|
| 473,200 A * | 4/1892 | Streeter | ............... 5/623 |
| 5,785,057 A | 7/1998 | Fischer | |
| 5,904,655 A | 5/1999 | Brackett | |
| 5,961,512 A | 10/1999 | Purnell | |
| 7,017,215 B1 | 3/2006 | Singer et al. | |
| 7,143,458 B2 | 12/2006 | Slater, Jr. | |
| 7,441,293 B1 | 10/2008 | Singer et al. | |
| 2002/0128577 A1 | 9/2002 | Smart | |
| 2005/0251076 A1 | 11/2005 | Branch | |
| 2008/0034502 A1 | 2/2008 | Copeland et al. | |
| 2008/0172791 A1 | 7/2008 | Walczyk | |
| 2008/0301878 A1 | 12/2008 | Elhabashy | |
| 2011/0048428 A1 | 3/2011 | Hunter, Jr. | |

FOREIGN PATENT DOCUMENTS

FR    2578417    9/1986

* cited by examiner

*Primary Examiner* — Kevin C Sirmons
*Assistant Examiner* — Ophelia A Hawthorne
(74) *Attorney, Agent, or Firm* — Waddey & Patterson, PC; Matthew C. Cox

(57) ABSTRACT

An arm stabilizer includes a stabilizer bar and one or more modular attachments that can be detachably secured to the stabilizer bar. A wrist support attachment can be secured to the distal end of the stabilizer bar. A reducer attachment can be secured to the stabilizer bar between the wrist support attachment and the proximal end of the stabilizer bar. The reducer attachment includes a telescoping post with a rest plate that provides a support for applying reduction force to the arm. The reducer attachment can be moved along the length of the stabilizer bar at various angular orientations. A removable wrist pad and a removable brace pad are also provided. In some embodiments stabilizer bar is pivotable about a base to allow the stabilizer bar with attachments to be pivoted away from the patient and repositioned at various points in space during use.

4 Claims, 14 Drawing Sheets

ARM STABILIZER DEVICE AND METHODS

CROSS-REFERENCE TO RELATED APPLICATION

This patent application is a continuation-in-part of and claims priority to U.S. patent application Ser. No. 12/550,701 filed Aug. 31, 2009 and entitled Arm Stabilizer for Elbow Surgical Procedure.

BACKGROUND

1. Technical Field

The present invention relates generally to orthopedic positioning devices and more particularly to devices and methods for supporting an arm before, during or after a surgical, rehabilitative or imaging procedure.

2. Background Art

Surgical procedures on the extremities of humans occur with great frequency, and particularly surgeries on the arm, elbow, and hand. Injuries to a person's arm, elbow and hand come frequently from falls, reaching to catch one's self, slipping or landing on an elbow causing a shattering or dislocation of the bone structure within the elbow, and attempting to brace oneself in response to a fall resulting in fractured bones in the humerus, elbow, forearm, and/or hand.

During the course of procedures to repair the broken bones or other features in the arm, historically, the patient's arm has been placed on a pillow or some other support structure resting on the patient's waist or chest, or a foam pad can be used to support the arm. This procedure fails to properly secure and maintain in a fixed position the extremity on which the procedure is being conducted. There have been numerous attempts to address this problem, including those described and illustrated in U.S. Pat. Nos. 473,200; 5,785,057; 7,017,215; 7,143,458; 7,441,293 and U.S. Publication No. 2008/0301878. The prior devices that are available in the industry, including those described in the aforesaid patents are an improvement over the simple use of a pillow resting on the patient's chest, but remain inadequate. Specifically, conventional products fail to provide good exposure to the extremity, particularly to the patient's elbow, and make it difficult for the surgeon and assistants to have easy, unfettered access to the patient's elbow to properly complete the surgical, rehabilitative or imaging procedure.

Thus, there is a continuing need in the art for improvements in devices and methods for supporting an arm for such purposes.

BRIEF SUMMARY

The present invention generally provides a device and associated methods for stabilizing an arm during a surgical or rehabilitative procedure, during resting, during medical imaging of the arm or during other times when it is necessary to have an arm stabilized in a stationary position. The device includes a stabilizer bar and several attachments that can be detachably secured to the stabilizer bar. Each attachment is also included as a part of the invention.

One aspect of the present invention provides an apparatus for stabilizing an arm. The apparatus includes a stabilizer bar including a proximal bar end and a distal bar end. A reducer attachment is securable to the stabilizer bar between the proximal bar end and the distal bar end. The reducer attachment includes a lateral rod, a sleeve extending upward from the lateral rod, a post slidably disposed in the sleeve, the post including an upper post end, and a rest plate disposed on the upper post end.

Another aspect of the present invention provides an arm stabilizer apparatus. The apparatus includes a stabilizer bar having a proximal bar end and a distal bar end. A wrist support attachment is attached to the stabilizer bar. The wrist support attachment includes a curved wrist support guide defining a guide channel. A wrist support block is disposed in the guide channel. The wrist support block is angularly moveable along the guide channel.

A further aspect of the present invention provides an arm stabilizer apparatus for clamping to a mounting structure. The apparatus includes a stabilizer bar having a distal bar end and a proximal bar end. A reducer attachment is detachably secured to the stabilizer bar between the distal bar end and the proximal bar end. A wrist support attachment is detachably secured to the stabilizer bar between the reducer attachment and the distal bar end. The wrist support attachment includes a guide bar slidably disposed on the stabilizer bar and a wrist support guide attached to the stabilizer bar. A base is pivotally attached to the stabilizer bar at a base hinge. The base includes a lateral rail and a vertical extension protruding generally upwards from the lateral rail. The base hinge is formed between the proximal bar end and the vertical extension.

A further embodiment of the present invention provides a reducer attachment apparatus for attachment to a stabilizer bar on device for supporting a human arm. The attachment includes a bar clamp, a lateral rod extending from the bar clamp, a sleeve extending upward from the lateral rod, a post disposed in the sleeve, the post including a free upper post end, and a rest plate attached to the upper post end. The rest plate provides a support for applying a reduction force to the arm.

A further embodiment of the present invention provides a wrist support attachment apparatus for attachment to a stabilizer bar on a device for stabilizing a human arm. The attachment includes a guide bar defining a guide bar socket shaped for receiving the stabilizer bar. A wrist support guide is attached to the guide bar. The wrist support guide defines a concave guide channel.

In a further embodiment, the present invention provides a removable wrist pad apparatus for attachment to a wrist support guide on a device for stabilizing a human arm. The apparatus includes a wrist pad defining a wrist recess; an outer panel attached to the wrist pad; and a wrist pad slot defined between the outer panel and the wrist pad.

In a further embodiment, the present invention provides a removable humerus pad apparatus for attachment to an arm brace on a device for stabilizing a human arm. The apparatus includes a humerus pad body; a pad panel attached to the humerus pad body; and a brace slot defined between the humerus pad body and the pad panel. The brace slot is shaped for receiving the arm brace.

Numerous other objects, features and advantages of the present invention will be readily apparent to those skilled in the art upon a reading of the following disclosure when taken in conjunction with the accompanying drawings.

DETAILED DESCRIPTION

Figure 1:
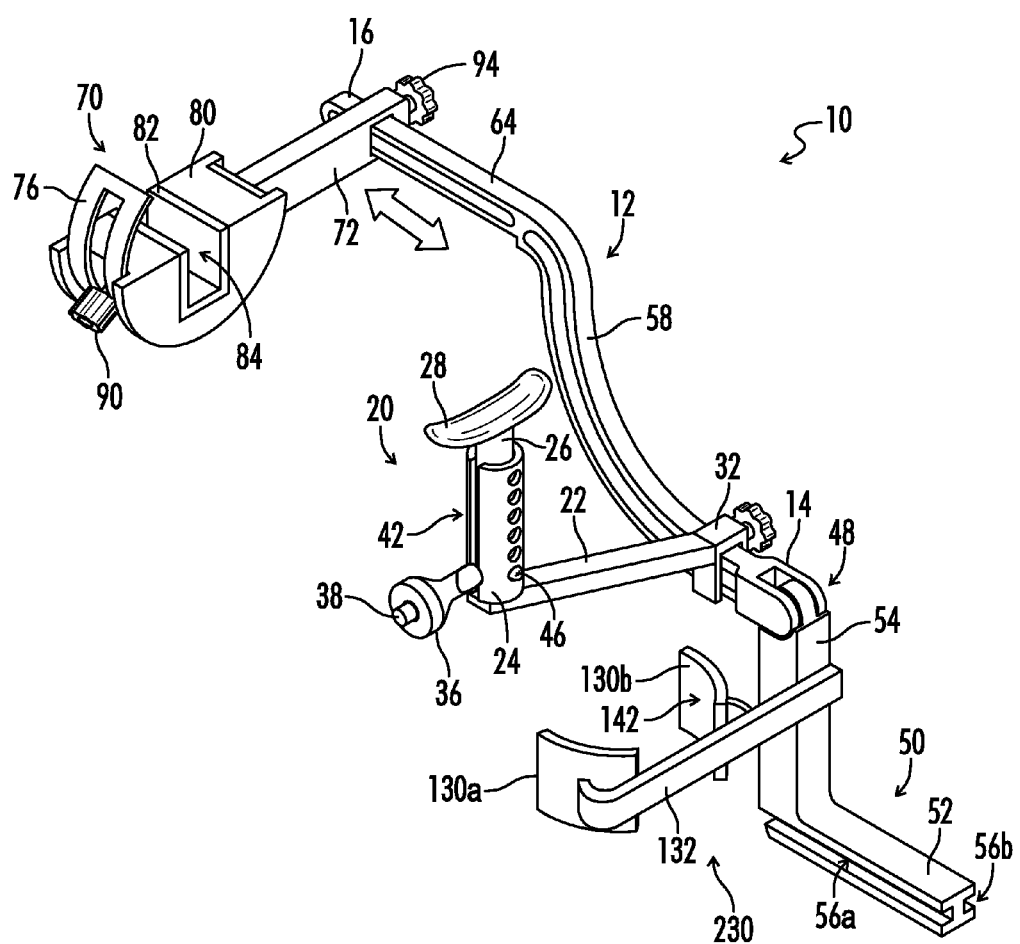
FIG. 1 illustrates a perspective view of an embodiment of an arm stabilizer in accordance with the present disclosure.

Referring now to the drawings, FIG. 1 illustrates a perspective view of an embodiment of an arm stabilizer generally designated by the numeral 10. In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

Referring further to FIG. 1, an embodiment of an arm stabilizer 10 includes a stabilizer bar 12 and a base 50. Stabilizer bar 12 is pivotally attached to base 50 at a first pivoting joint 48. Stabilizer bar 12 includes a proximal bar end 14 and a distal bar end 16. One aspect of the present disclosure provides an arm stabilizer 10 that can include one or more modular components releasably attached to the stabilizer bar 12 between proximal bar end 14 and distal bar end 16. For example, as seen in FIG. 1, a wrist support attachment 70 can be attached to stabilizer bar 12. Also, a reducer attachment 20 can be attached to stabilizer bar 12 between the wrist support attachment 70 and the proximal bar end 14. Generally, during use, the wrist support attachment 70 includes a wrist recess 84 shaped for receiving a patient's wrist, arm or hand. The patient's wrist can be positioned in wrist recess 84, and reducer attachment 20 can engage the patient's upper or lower arm at a position near the elbow joint. A third modular component includes a brace pad attachment 230 that can be detachably secured to base 50 on arm stabilizer 10.

Referring further to FIG. 1, wrist support attachment 70 is a modular attachment that can be detachably secured to stabilizer bar 12. Wrist support attachment 70 generally allows a surgeon or operator to control the rotational position of a patient's wrist, arm or hand during a surgical or rehabilitative procedure. By controlling the patient's wrist, arm or hand orientation, the bones of the patients wrist, arm or hand, including a patient's radius and ulna, can be positioned in a desirable orientation. Additionally, it may be necessary to angularly reposition the wrist one or more times during a surgical procedure or operation. The wrist support attachment 70 makes such in situ repositioning possible.

Figure 2:
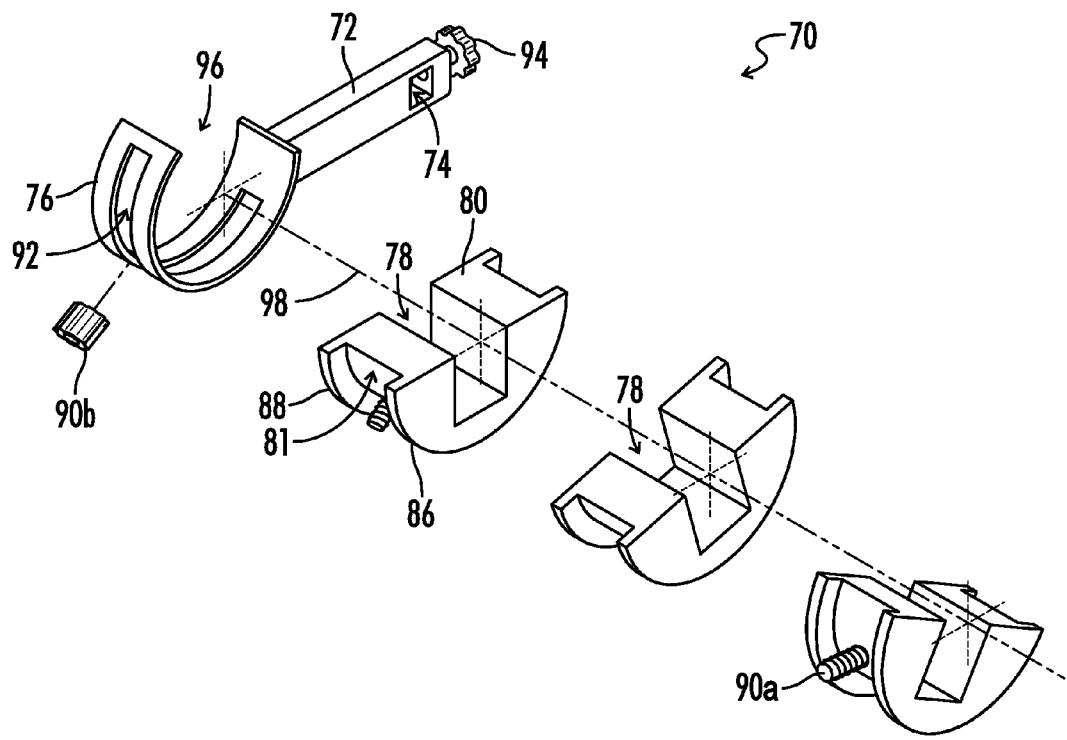
FIG. 2 illustrates a partially exploded view of an embodiment of a wrist support attachment for attachment to an arm stabilizer in accordance with the present disclosure, illustrating a wrist support block rotatable in different positions about a block rotation axis.
Figure 3:
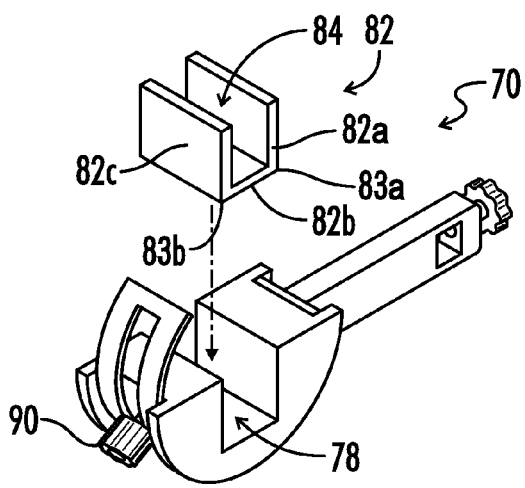
FIG. 3 illustrates a partially exploded view of an embodiment of a wrist support attachment for attachment to an arm stabilizer in accordance with the present disclosure.
Figure 6:
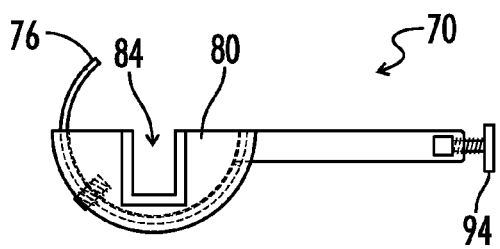
FIG. 6 illustrates a front elevation view of an embodiment of a wrist support attachment with a wrist support block in a first angular position.
Figure 7:
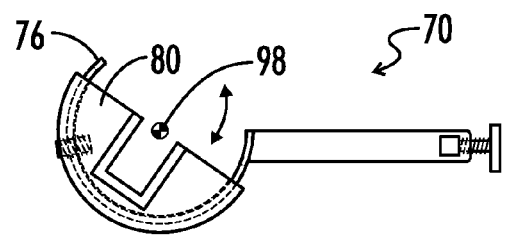
FIG. 7 illustrates a front elevation view of the embodiment of a wrist support attachment of FIG. 6 with the wrist support block in a second angular position.

Referring to FIG. 1, wrist support attachment 70 generally includes a wrist recess 84. Wrist recess 84 is generally positioned and shaped for receiving a patient's wrist, arm or hand. Wrist recess 84 can include a concave shape, and a patient's wrist, arm or hand can be positioned in the wrist recess 84 so that the patient's fingers extends generally away from arm stabilizer 10. In some embodiments, such as those illustrated in FIGS. 2-7, a wrist support attachment 70 includes a guide bar 72 and a wrist support guide 76. Wrist support guide 76 includes guide channel 96. Guide channel 96 can include a curved, or arcuate, shape, as seen in FIG. 2 in some embodiments. In additional embodiments, guide channel 96 can include a rectangular, polygonal or another curvilinear shape not shown. A wrist support block 80 can be positioned in guide channel 96. Wrist support block 80 includes a curved outer surface 81 generally shaped to correspond to the curvature profile of wrist support guide 76. As seen in FIG. 3, wrist support block 80 can be disposed in guide channel 96 on wrist support guide 76 such that wrist support block 80 can assume various angular positions when disposed in wrist support guide 76, as seen in FIG. 2 and FIGS. 6 and 7.

Referring further to FIG. 2, in some embodiments an angular guide slot 92 is defined in wrist support guide 76. Guide slot 92 can include an angular clearance void extending through the thickness of wrist support guide 76. Guide slot 92 can include an angular void extending across an angular range. In some embodiments, the guide slot angular range is between about zero and about three-hundred degrees. In another embodiment, guide slot angular range is about two-hundred-thirty degrees. Referring further to FIG. 1, a support fastener 90 can be attached to wrist support block 80 for securing wrist support block 80 in a desired angular orientation relative to wrist support guide 76. Support fastener 90 in some embodiments includes a threaded post 90a extending substantially radially from curved outer surface 81 on wrist support block 80, seen in FIG. 2. Threaded post 90a extends through guide slot 92 in some embodiments so that, as wrist support block 80 is angularly positioned, threaded post 90a translates through guide slot 92. When wrist support block 80 is aligned at a preferred angular orientation, a threaded nut 90b can be threadedly engaged with threaded post 90a and tightened against wrist support guide 76 such that wrist support guide 76 is clamped between wrist support block 80 and threaded nut 90b. As such, wrist support block 80 can be releasably secured in place at a desired angular orientation relative to wrist support guide 76. In some embodiments, threaded nut 90b includes a textured knob allowing a surgeon or operator to loosen fastener 90, change the angular position of wrist support block 80, and then re-tighten fastener 90 at the new angular position. In some applications, this can be achieved by the surgeon or operator using only one hand. By changing the angular position of the wrist support block 80, the surgeon or operator can reposition the patient's wrist, arm or hand, which in turn changes the position of one or more bones extending from the wrist to the elbow joint. As seen in FIG. 2, in some embodiments, the wrist support block 80 is generally angularly moveable about a block rotation axis 98.

In other embodiments not shown, support fastener 90 can include a threaded screw or bolt inserted through guide slot 92 and threadedly engaging a corresponding threaded hole defined in wrist support block 80. In such embodiments, support fastener 90 can be tightened against wrist support guide 96, thereby clamping wrist support guide 96 between a head on support fastener 90 and releasably securing wrist support block 80 at a desired angular position.

Figure 4:
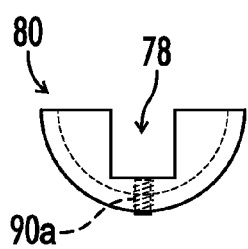
FIG. 4 illustrates a front elevation view of an embodiment of a wrist support block.

As seen in FIG. 4, in some embodiments, threaded post 90a can extend directly downward from the wrist support cavity 78. Wrist support cavity 78 generally forms a recess in which the patient's wrist or arm can be received. As seen in FIGS. 2, 6 and 7, in additional embodiments, threaded post 90a can extend in an offset orientation relative to the wrist support cavity 78.

Figure 5:
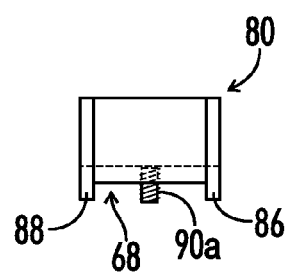
FIG. 5 illustrates a side elevation view of the embodiment of a wrist support block of FIG. 4.

As seen in FIGS. 2 and 5, wrist support block 80 in some embodiments includes one or more block flanges extending radially outward from wrist support block 80. For example, a first block flange 86 extends substantially radially outward from wrist support block 80 and more specifically from curved outer surface 81. First block flange 86 generally extends in the radial direction away from block rotation axis 98 at least partially beyond the inner edge of wrist support guide 76. As such, first block flange 86 is operable to prevent axial movement of the wrist support block 80 relative to the wrist support guide 76. Wrist support block 80 includes a semi-cylindrical profile in some embodiments.

In some embodiments, a second block flange 88 extends substantially outward from wrist support block 80. Second block flange 88 generally extends in the radial direction away from block rotation axis 98 at least partially beyond the inner edge of wrist support guide 76. As such, second block flange 88 is operable to prevent axial movement of the wrist support block 80 relative to the wrist support guide 76.

In some embodiments, a flange gap 68, seen in FIG. 5, is formed between first and second block flanges 86, 88. The curved wrist support guide 76 is at least partially received in the flange gap 68 when wrist support block 80 is positioned in the guide channel 96 in some embodiments.

Referring further to FIGS. 1-7, wrist support attachment 70 can be modularly attached to, or is detachably securable to, an arm stabilizer 10, and more specifically to a stabilizer bar 12 on an arm stabilizer 10, using a releasable attachment. A guide bar 72 is attached to wrist support guide 76. Guide bar 72 includes a guide bar socket 74. Guide bar socket 74 forms an opening in guide bar 72 through which a portion of stabilizer bar 12 can be received. For example, in some embodiments guide bar socket 74 is formed by a hole defined in guide bar 72. Guide bar 72 can be attached to distal bar end 16 by sliding distal bar end 16 into the guide bar socket 74. Once positioned on stabilizer bar 12, the guide bar 72 can be repositioned along the length of stabilizer bar 12. In some embodiments, stabilizer bar 12 includes a linear guide track region 64. The linear guide track region 64 generally forms a substantially linear region on stabilizer bar 12 near distal bar end 16. As guide bar 72 is moved along linear guide track region 64, the position of wrist support attachment 70 relative to proximal bar end 14 can be adjusted. Once a desired position of guide bar 72 along stabilizer bar 12 is reached, in some embodiments, guide bar 72 can be releasably secured in place using a guide bar fastener 94 attached to guide bar 72. In some embodiments, guide bar fastener 94 includes a threaded bolt or a screw threadedly inserted through a threaded hole formed on or attached to guide bar 72. A portion of the guide bar fastener 94 extends partially into the guide bar socket 74 and engages stabilizer bar 12 when guide bar fastener 94 is tightened. When guide bar fastener 94 is fully or partially released, guide bar 72 is at least partially disengaged from stabilizer bar 12, and guide bar 72 can be repositioned along the length of stabilizer bar 12. In some embodiments, guide bar fastener 94 includes a textured or knurled knob for facilitating manual tightening and loosening of guide bar fastener 94 relative to stabilizer bar 12.

Referring further to FIG. 1 and FIG. 3, in some embodiments, a wrist pad 82 is removably disposed in wrist support cavity 78. Wrist pad 82 can include a dissimilar material as wrist support block 80. In some embodiments, wrist pad 82 can include a flexible material such as but not limited to a closed or open cell foam, a padding material, a textile material, a gel material, or other types of suitable materials known in the art. Wrist pad 82 is generally shaped to correspond to the shape of wrist support cavity 78. Although wrist pad 82 and wrist support cavity 78 are illustrated in FIGS. 1-7 as having a generally rectangular shape, it will be readily appreciated by those of skill in the art that wrist pad 82 and/or wrist support cavity 78 can include other linear or curvilinear shapes such as semi-circular or semi-elliptical shapes.

Also seen in FIG. 3, wrist pad 82 can include a single piece of material folded at a first fold 83a and at a second fold 83b to form a first pad panel 82a, a second pad panel 82b positioned between first and second folds 83a, 83b, and a third panel 82c. In additional embodiments, wrist pad 82 can be integrally formed on wrist support block 80 using any variety of suitable material forming techniques such as but not limited to overmolding or injection molding. In some embodiments, wrist support block 80 includes a polymer or a plastic material, and wrist pad 82 is formed directly on wrist support block 80. In additional embodiments, wrist pad 82 may be adhered to wrist support block 80.

Figure 17:
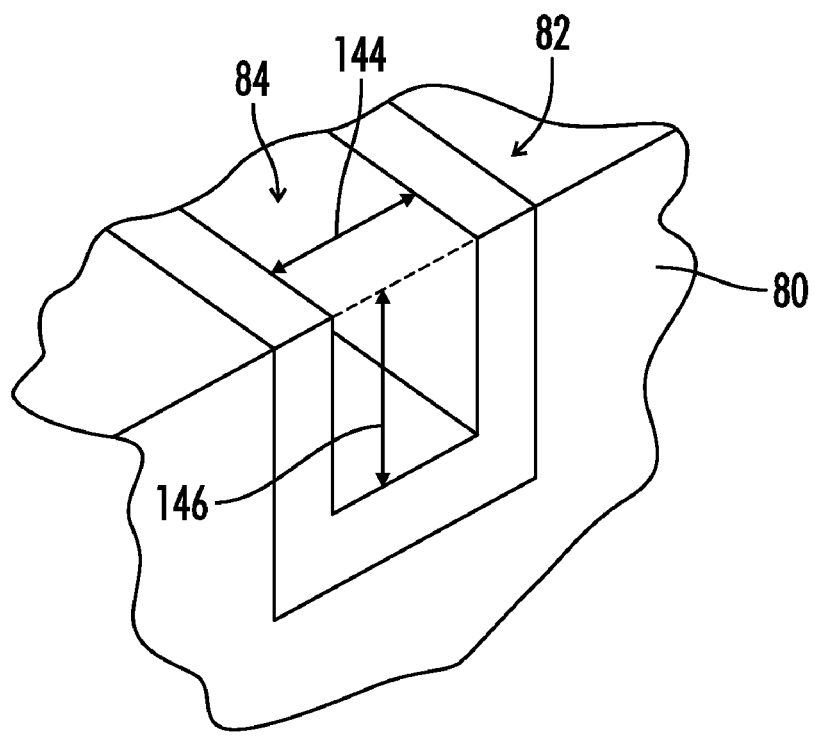
FIG. 17 illustrates a detail partial perspective view of an embodiment of a wrist pad on a wrist support block in accordance with the present disclosure.

A wrist recess 84 is formed by wrist pad 82. Wrist recess 84 forms an opening for positioning a patient's wrist, arm or hand. Referring now to FIG. 17, in some embodiments, wrist pad 82 defines a wrist recess 84 having a wrist recess width 144 and a wrist recess depth 146. In some embodiments, it is desirable to provide a wrist pad 82 forming a wrist recess 84 dimensioned such that a patient's wrist, arm or hand cannot rotate freely within wrist recess 84. To accomplish this objective, wrist recess width 144 and wrist recess depth 146 can be chosen to limit free rotation of a patient's wrist, arm or hand in wrist recess 84.

Figure 18:
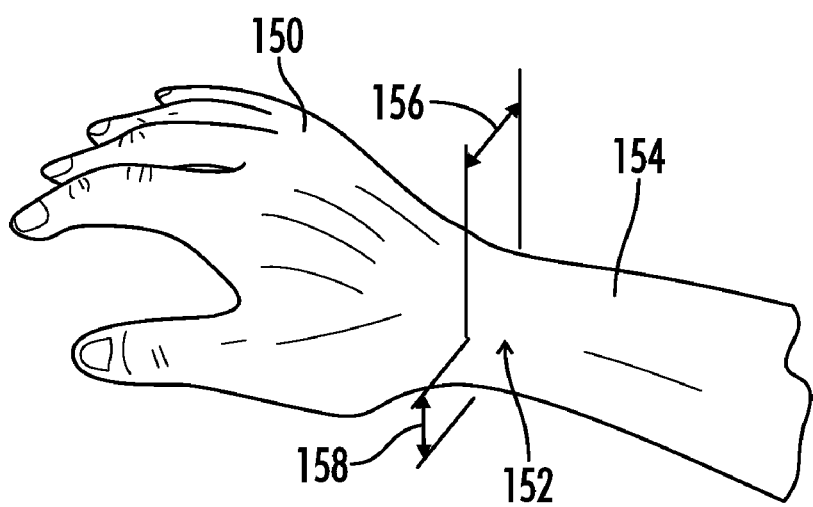
FIG. 18 illustrates a perspective view of an embodiment of a patient's wrist.

As seen in FIG. 18, in some embodiments, a wrist 152 positioned between a patient's arm 154 and hand 150 generally includes a thickness 158 and a width 156. Wrist recess 84 can generally be dimensioned such that the wrist thickness 158 corresponds to the wrist recess width 144. As such, the wrist 152 can be inserted into the wrist recess 84 in an orientation where the thumb generally points upward or downward. Similarly, the wrist recess depth 146 can correspond to the wrist width 156. As such, the wrist, arm or hand can be generally prevented from freely rotating in the wrist recess 84. In some embodiments, wrist pad 82 is formed such that the ratio of the wrist recess depth 146 to wrist recess width 144 is greater than one. In such embodiments, when the wrist support block 80 is rotated relative to wrist support guide 76, wrist, arm and/or hand orientation is forcefully rotated generally about block rotation axis 98, or about an axis substantially parallel to block rotation axis 98.

In some embodiments, the angular position of the patient's wrist, arm or hand can be repositioned in real time during a surgery or a procedure by adjusting the angular position of the wrist support block 80.

Figure 8:
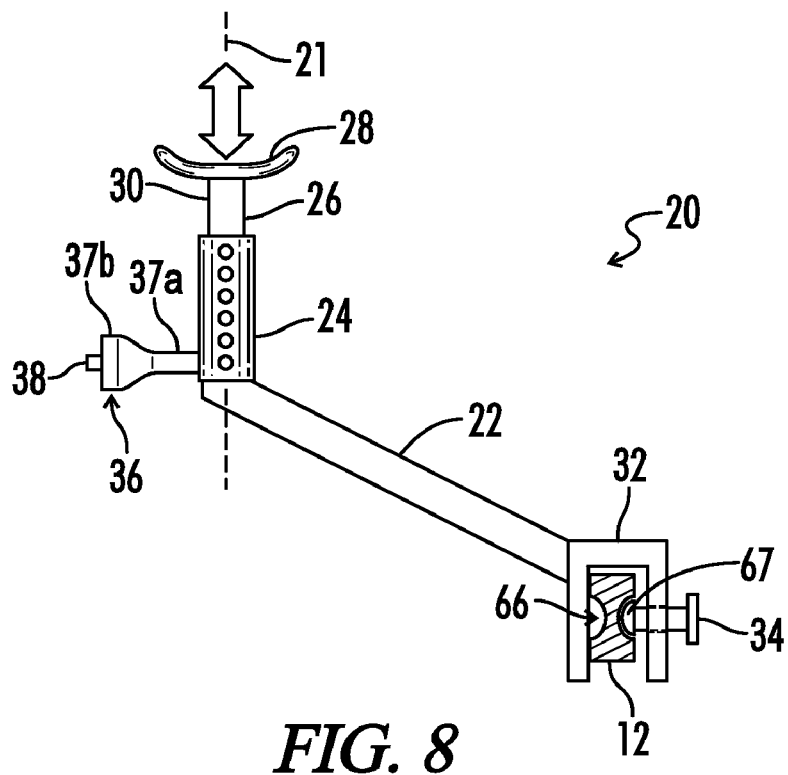
FIG. 8 illustrates a front elevation view of an embodiment of a reducer attachment mounted on a stabilizer bar in accordance with the present disclosure.
Figure 9:
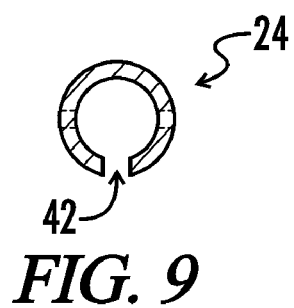
FIG. 9 illustrates a partial cross-sectional view of an embodiment of a sleeve of a reducer attachment in accordance with the present disclosure.

Referring again to FIG. 1, a reducer attachment 20 forms another modular attachment that can be installed on stabilizer bar 12. It is noted that arm stabilizer 10 can function with or without reducer attachment 20. Reducer attachment 20 is releasably connected to stabilizer bar 12 using a bar clamp 32. Bar clamp 32 in some embodiments includes a U-shaped clamp shaped for receiving stabilizer bar 12. As seen in FIG. 8, a bar clamp fastener 34 is attached to bar clamp 32. In some embodiments, bar clamp fastener 34 includes a threaded screw or bolt having a knob for manually screwing bar clamp fastener 34 toward or away from stabilizer bar 12. When bar clamp fastener 34 is screwed toward and tightened against stabilizer bar 12, reducer attachment 20 can be fixed in place relative to stabilizer bar 12. When bar clamp fastener is screwed away from and at least partially released from engagement with stabilizer bar 12, reducer attachment 20 can be slid along the length of stabilizer bar 12 or removed entirely from stabilizer bar 12.

In some embodiments, stabilizer bar 12 includes one or more reducer grooves 66, seen in FIG. 8. A bar clamp fastener tip 67 disposed on the end of bar clamp fastener 34 nearest stabilizer bar 12 is received in a reducer groove 66 in some embodiments. In some embodiments, bar clamp fastener tip 67 includes a polymer material. When bar clamp fastener tip 67 is received in a reducer groove 66, bar clamp fastener 34 can be partially disengaged from stabilizer bar 12 such that reducer attachment 20 can be slid along stabilizer bar 12 without being fully disengaged from stabilizer bar 12. In some embodiments, stabilizer bar 12 includes a first reducer groove 66a defined on a first side of stabilizer bar 12, seen in FIG. 15, and a second reducer groove 66b defined on the second side of stabilizer bar 12, seen in FIG. 13. In such embodiments, reducer attachment 20 can be positioned to extend outward from either side of stabilizer bar because bar clamp fastener tip 67 can interchangeably engage first and second reducer grooves 66a, 66b, depending on the side of stabilizer bar 12 from which reducer attachment 20 projects.

Referring again to FIG. 8, a lateral rod 22 extends from bar clamp 32 and away from stabilizer bar 12. Lateral rod 22 can project away from bar clamp 32 at an upward angle in some embodiments, as seen in FIG. 8, or at a horizontal or a downward angle in other embodiments not shown. A sleeve 24 extends generally upward from lateral rod 22. Sleeve 24 in some embodiments includes a hollow sleeve having an opening at its upper axial end. A post 26 is slidably disposed in sleeve 24. Post 26 telescopingly engages sleeve 24. Post 26 includes an upper post end 30 extending from sleeve 24. A rest plate 28 is disposed on upper post end 30. Rest plate 28 can include a concave shape facing away from post 26 in some embodiments. In other embodiments, rest plate 28 can include a flat or non-concave shape not shown. Rest plate 28 provides a support for engaging a patient's arm. Post 26 is generally axially moveable in sleeve 24 along a reducer axis 21. Reducer axis 21 can be aligned with a patient's elbow joint in some applications.

In additional embodiments, reducer attachment 20 includes a lateral rod 22 and a fixed post 26 attached directly to the lateral rod 22 with a rest plate 28 disposed on the upper end of the post 26.

Figure 11:
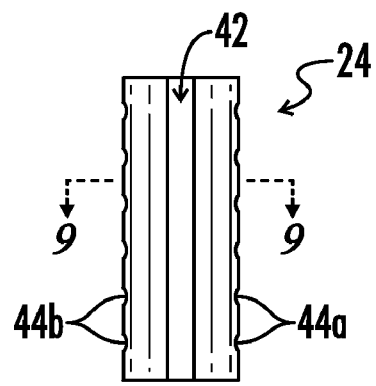
FIG. 11 illustrates a side elevation view of an embodiment of the sleeve of FIG. 9.

As seen in FIG. 1 and FIG. 11, sleeve 24 includes a sleeve opening 42. Sleeve opening 42 generally includes a vertical orientation. In some embodiments, sleeve opening 42 extends along the entire height of sleeve 24. In other embodiments, sleeve opening 42 extends only partially along the height of sleeve 24. A handle 36 is attached to post 26. Handle 36 extends from post 26 radially through sleeve opening 42. Handle 36 provides a means for manually moving post 36 and rest plate 28 up or down along reducer axis 21. Handle 36 includes a proximal handle end 37a and a distal handle end 37b, seen in FIG. 8. Proximal handle end 37a is attached to post 26, and distal handle end 37b extends away from post 26. In some embodiments, proximal handle end 37a includes a smaller handle diameter than distal handle end 37b. As such, a user is able to grasp distal handle end 37b in or near the palm of only one of the user's hands while receiving the proximal handle end 37a between two fingers. As such, handle 36 can be manipulated using only one hand in some embodiments.

Figure 10:
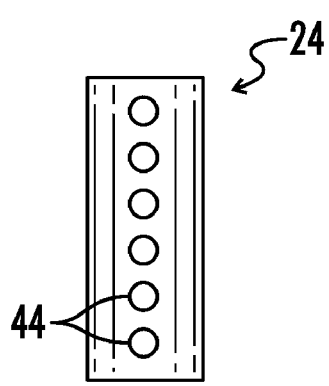
FIG. 10 illustrates a front elevation view of an embodiment of the sleeve of FIG. 9.

Referring again to FIG. 1, a control button 38 is disposed on the handle 36 in some embodiments. Control button 38 extends axially from distal handle end 37b. Also seen in FIG. 1 and FIG. 10, sleeve 24 includes a plurality of holes 44. Each hole is defined at an axial location along the height of sleeve 24. A latch 46 extends radially from post 26. Latch 46 can be attached to a spring mechanism for biasing latch 46 in a radially extended position, as seen in FIG. 1. In the radially extended position, latch 46 extends through one of the plurality of holes 44. Latch 46 is mechanically linked to control button 38 so that, by depressing control button 38, latch 46 is retracted radially inwardly such that latch 46 no longer extends fully through the hole. As such, latch 46 is configurable to selectively disengage at least one of the plurality of holes 44 defined in the sleeve 24 when the control button 38 is depressed. When control button 38 is depressed, post 26 can be moved along reducer axis 21 using handle 36. When post 26 is moved to the desired axial position relative to sleeve 24, control button 38 can be released and latch 46 extends radially outwardly. If, upon release of control button 38, latch 46 is not aligned with one of the plurality of holes 44, post 26 can be moved slightly up or down to align latch 46 with a nearest adjacent one of the plurality of holes 44 either above or below latch 46. Upon alignment of latch 46 with one of the plurality of holes 44 while control button 38 is not depressed, latch 46 will resiliently spring through the hole and will selectively lock post 26 at that axial position relative to sleeve 24. As such, the position of post 26 can be used to define a vertical position of rest plate 28 in some embodiments.

As seen in FIG. 11, in some embodiments, sleeve 24 includes holes on opposite sides of sleeve 24. For example, a first plurality of holes 44a is defined on a first side of sleeve 24, and a second plurality of holes 44b is defined on a second side of sleeve 24. Similarly, in some embodiments, latch 46 can include a first latch end extending through one of the first plurality of holes 44a and a second latch end extending through one of the second plurality of holes 44b. Each latch end is mechanically linked to control button 38 in such embodiments.

Referring further to FIG. 1, in some embodiments, sleeve 24 is integrally attached to lateral rod 22. In other embodiments, sleeve 24 can be mechanically attached to lateral rod 22 using a mechanical fastening means such as but not limited to welding, using a fastener or a threaded engagement, or using an adhesive.

In some embodiments, reducer attachment 20 is operable to provide a support for applying a reduction force to an arm. A reduction force is generally referred to as a force that a surgeon or operator may seek to apply against a patient's arm for aligning one or more structures within the arm, such as a bone, a joint, a ligament or a tendon. The application of a reduction force against a patient's upper or lower arm can be necessary during surgery or rehabilitation operations to properly align the structures inside the arm. Using conventional techniques, a surgeon or an assistant would typically apply force on opposing sides of the arm using both of the surgeon's or the assistant's hands. The conventional bimanual technique for application of reduction force makes concurrent surgical operation or other procedures on the joint during periods of reduction force application difficult. The reducer attachment 20 of the present invention can be used in some embodiments to replace one of the surgeon's or operator's hands used for reduction force application. For example, when rest plate 28 is positioned to engage the patient's arm at or near the elbow joint, a surgeon or operator can use one hand to press against the region of the arm necessary to apply the desired reduction force while the rest plate 28 supports the arm. As such, the surgeon or operator uses the rest plate 28 as a backing plate for force application using only one of the surgeon's or operator's hands. The remaining hand of the surgeon or operator is then free to perform a task simultaneous with the reduction force application.

Figure 12:
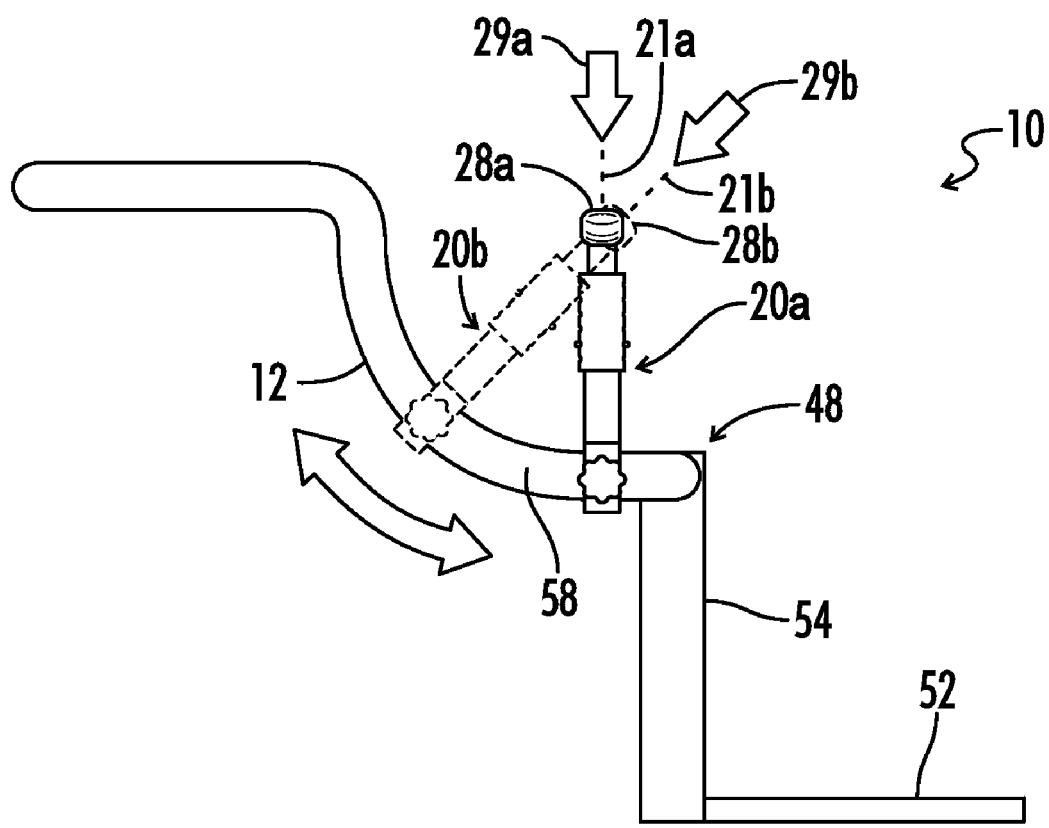
FIG. 12 illustrates a side elevation view of an embodiment of an arm stabilizer illustrating a moveable reducer attachment in accordance with the present disclosure.

One aspect of the present disclosure provides a reducer attachment 20 that can slide along the stabilizer bar 12. Generally, reduction force is at times most effective when applied in a direction along the reducer axis 21. Because the stabilizer bar includes a curved stabilizer bar region 58, seen in FIG. 1 and FIG. 12, the reducer axis 21 orientation can be adjusted by moving the reducer attachment 20. Thus, the surgeon or operator can position the reducer attachment 20 such that the direction of reduction force application 29 can be aligned with reducer axis 21. In many applications, it is desirable to apply reduction force in different directions. For example, as seen in FIG. 12, in a first reducer attachment position 20a, the direction of reduction force 29a is aligned with a first reducer axis orientation 21a. In this embodiment, reduction force 29a can be applied generally parallel to the orientation of the humerus. Also seen in FIG. 12, reducer attachment 20 can be moved to a second reducer attachment position 20b along stabilizer bar 12, causing the orientation of reducer axis 21 to move to a second reducer axis orientation 21b. In this position, a second reduction force 29b can be applied against the patent's arm in a different direction. Using the reducer attachment apparatus 20, reduction force can be applied in a direction parallel to the shaft of the radius and ulna, parallel to the shaft of the humerus, or in any direction in between.

Figure 15:
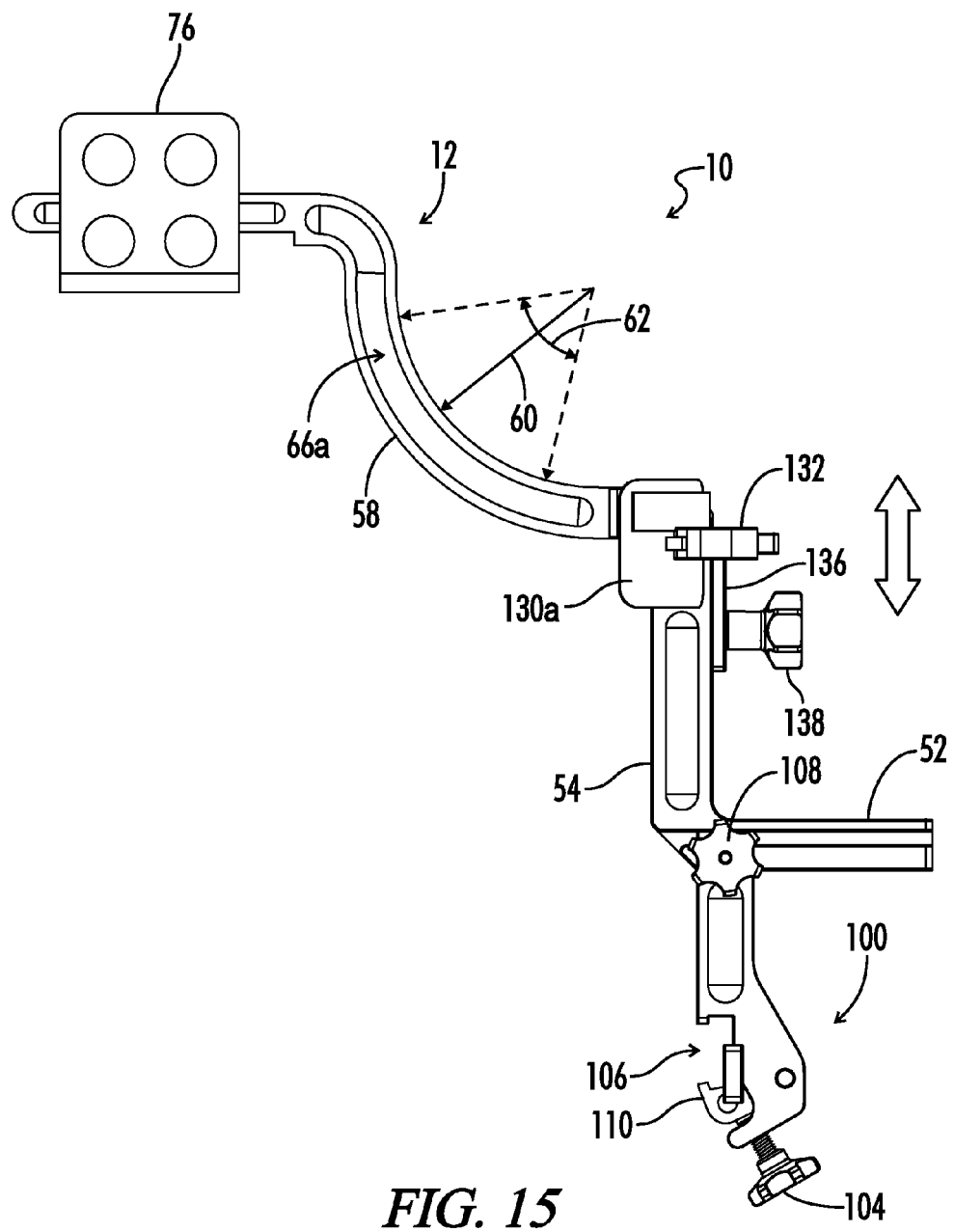
FIG. 15 illustrates a side elevation view of the embodiment of an arm stabilizer of FIG. 13 having a stabilizer bar in a downward position.

Referring now to FIG. 12 and FIG. 15, in some embodiments, the stabilizer bar 12 includes a curved stabilizer bar region 58 that includes a radius of curvature 60. The radius of curvature 60 in some embodiments extends across a radius angle 62. In some embodiments, radius angle 62 is between about forty-five and about ninety degrees. In other embodiments, radius angle 62 is greater than or less than this angular range. Radius of curvature 60 can be nonuniform across radius angle 62 so stabilizer arm 12 can accommodate different patients having different humerus lengths. In such embodiments, when reducer attachment 20 is translated across the curved region of stabilizer bar 12, rest plate 28 translates in space. In other embodiments, radius of curvature 60 can remain constant across all or part of radius angle 62. In such embodiments, when reducer attachment 20 is translated across the curved region of stabilizer bar 12 corresponding to a constant radius of curvature, rest plate 28 stays substantially in the same position in space and rotates about the vertex of the radius angle. Rest plate 28 generally assumes a first rest plate position 28a corresponding to the first reducer attachment position and a second rest plate position 28b corresponding to the second reducer attachment position, as seen in FIG. 12. When reducer attachment 20 is repositioned on stabilizer bar 12 along the constant radius portion of the curved stabilizer bar region 58, the rest plate can remain in substantially the same position, corresponding to the elbow joint. As such, rest plate continues to support the elbow joint as the reducer attachment 20 is moved angularly relative to stabilizer bar 12.

Figure 13:
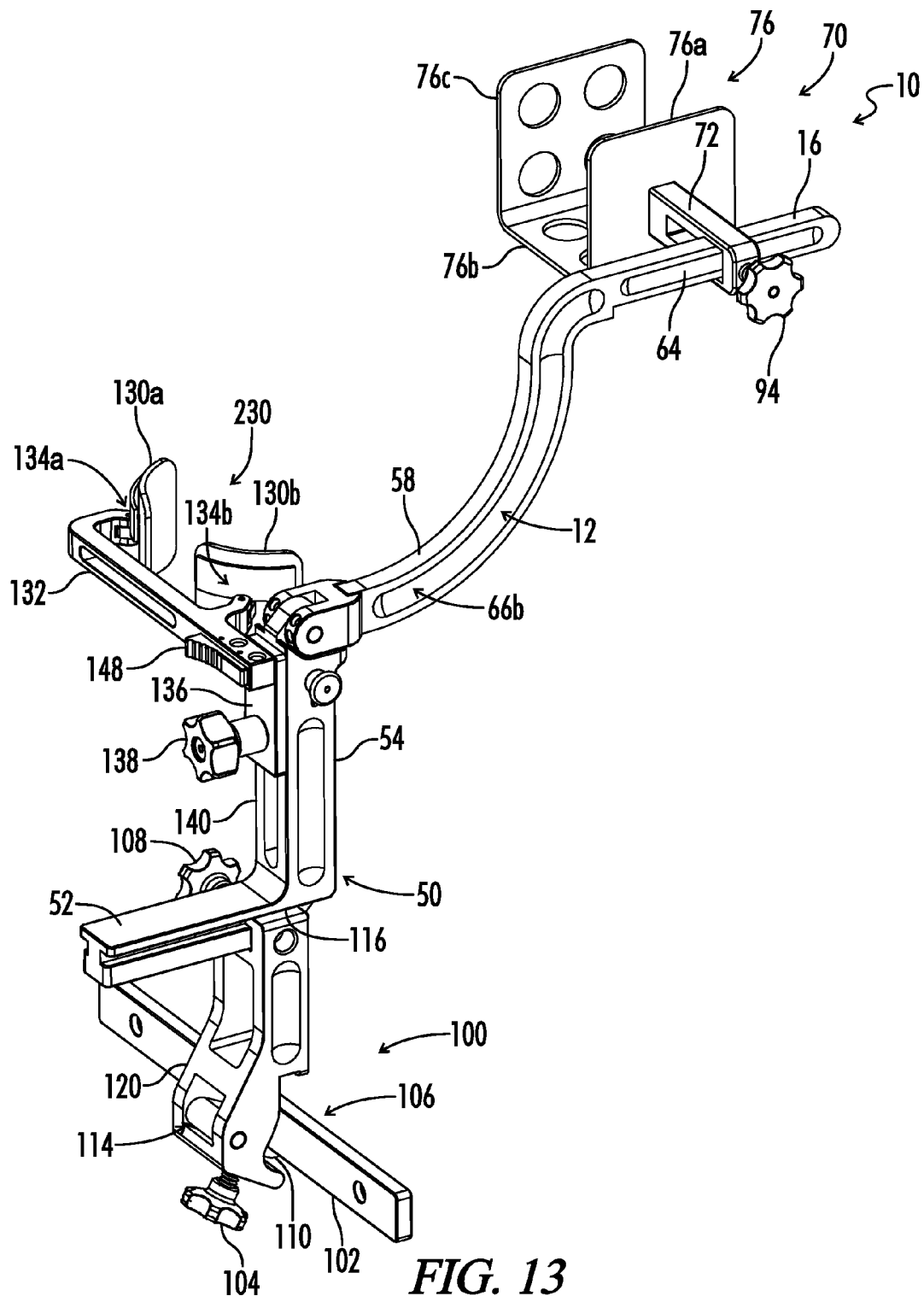
FIG. 13 illustrates a perspective view of an alternative embodiment of an arm stabilizer in accordance with the present disclosure.

Also seen in FIG. 13, an alternative embodiment of a wrist support attachment 70 includes a wrist support guide 76 having a rectangular shape. Wrist support guide 76 includes a first guide panel 76a, a second guide panel 76b and a third guide panel 76c. First and third guide panels 76a and 76c generally project upwards from second guide panel 76b. Wrist support guide 76 is attached to a guide bar 72 that is releasably securable at various positions to stabilizer bar 12.

Figure 19:
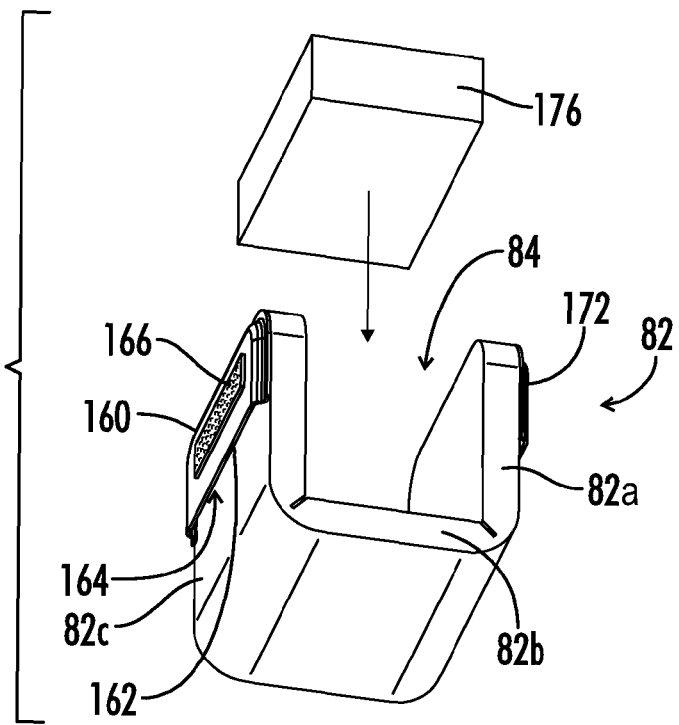
FIG. 19 illustrates a partially exploded perspective view of an embodiment of a wrist pad with a wrist pad slot in accordance with the present disclosure.

A removable wrist pad 82, seen in FIG. 19, can be attached directly to wrist support guide 76 in some embodiments. Wrist pad 82 in this embodiment includes first, second and third wrist pad panels 82a, 82b, 82c integrally attached at a plurality of wrist pad folds 83a, 83b, seen in FIG. 3. An outer panel 160 is disposed on a wrist pad panel on wrist pad 82. Outer panel 160 and the corresponding wrist pad panel to which it is attached form a wrist pad slot 164. Wrist pad slot 164 includes a space defined between outer panel 160 and its corresponding wrist pad panel. An opening to the wrist pad slot 164 is defined along the lower edge 162 of outer panel 160 such that the wrist pad 82 can be slid onto at least one of the guide panels 76a, 76b, 76c, seen in FIG. 13, from above. When wrist pad 82 is slid onto wrist support guide 76, an upright guide panel of wrist support guide 76 is received in the wrist pad slot 164 between the wrist pad 82 and the outer panel 160. A second outer panel 172 can be positioned on the opposite side of wrist pad 82, forming a second wrist pad slot for receiving a second upright guide panel of wrist support guide 76. As seen in FIG. 19, a removable pad block 176 can be disposed between wrist pad panels from above.

Figure 20:
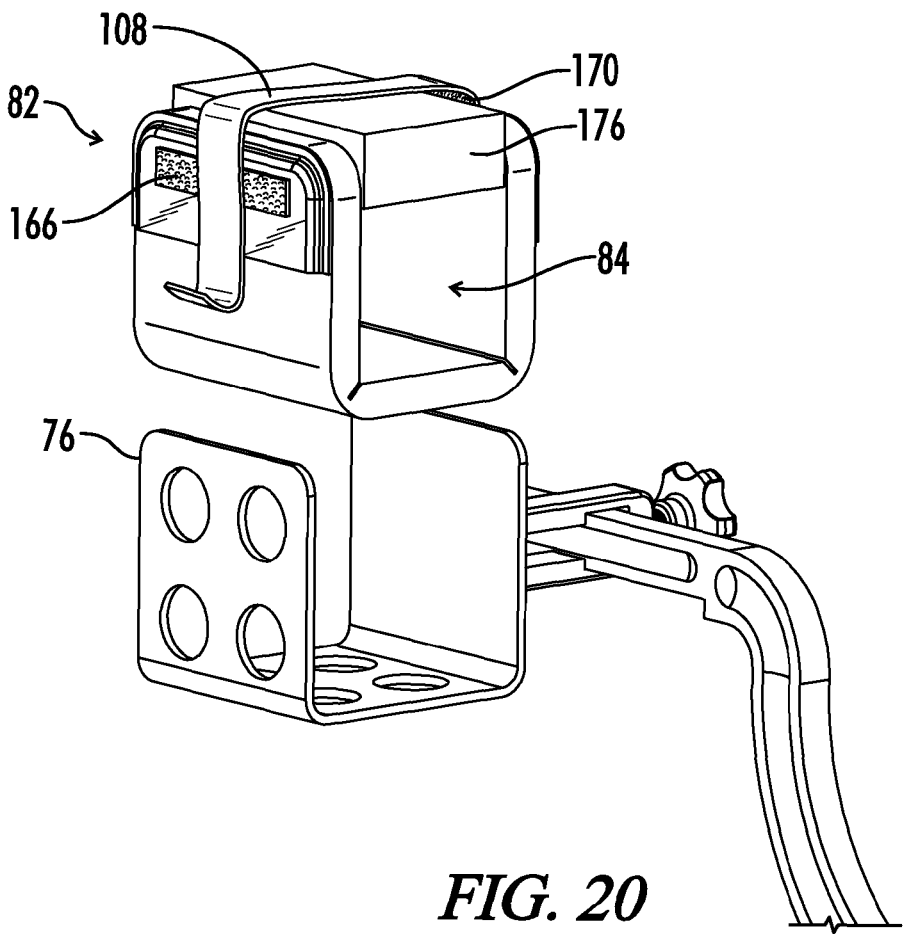
FIG. 20 illustrates a partially exploded perspective view of an embodiment of a wrist pad including a wrist strap positioned for engagement with a wrist support guide in accordance with the present disclosure.

One advantage of the embodiment of a wrist pad 82 illustrated in FIG. 19 is that the wrist pad 82 can be secured to a patient's wrist, arm or hand prior to engagement of wrist pad 82 with the arm stabilizer 10. In some embodiments, a patch 166 is positioned on wrist pad 82. Patch 166 in one embodiment is positioned on outer panel 160. Patch 166 in some embodiments includes a fastener such as a hook-and-loop fastener material. A wrist strap 108, seen in FIG. 20, can be positioned on wrist pad 82 such that wrist strap inner surface 170 contacts patch 166. Wrist strap inner surface 170 also includes a fastener such as a corresponding hook-and-loop fastener material in some embodiments. During use, a patient's wrist, arm or hand can be inserted in wrist recess 84 and then wrist strap 108 can be fastened to wrist pad 82 across the top of wrist recess 84, spanning the wrist recess 84, as seen in FIG. 20, to secure the patient's wrist, arm or hand to wrist pad 82. Pad block 176 can be positioned between the patient's wrist, arm or hand and wrist strap 108. After the pad is installed on the patient's wrist, arm or hand, the pad can then be slid onto the wrist support guide 76. In alternative embodiments, the wrist pad 82 can be positioned on the wrist support guide 76 prior to positioning the patient's wrist, arm or hand in wrist recess 84. Such modular assembly of wrist pad 82 on wrist support attachment 70 also allows the wrist, arm or hand to be disengaged from arm stabilizer 10 without removing wrist pad 82.

In some embodiments, wrist pad 82 includes a foam material. Wrist pad 82 can be a disposable part of the arm stabilizer system. By providing a disposable wrist pad 82, arm stabilizer 10 can be used with multiple patients while providing sanitary skin contact between arm stabilizer 10 and each new patient.

Referring again to FIG. 1, a brace pad attachment 230 can be detachably secured to arm stabilizer 10. In some embodiments, brace pad attachment 230 is detachably securable to vertical extension 54 on base 50. Brace pad attachment 230 includes one or more arm braces 130a, 130b attached to an arm brace bracket 132. Arm brace bracket 132 extends laterally from base 50. In some embodiments, each arm brace 130a, 130b, includes a curved brace surface 142 shaped to engage a patient's arm. Each arm brace 130 may be referred to as a humerus brace in some embodiments because each arm brace 130 is positioned to engage a region of the patient's arm surrounding or near the humerus bone. In the embodiment seen in FIG. 1, first and second arm braces 130a, 130b are positioned to engage the tricep side of a patient's upper arm when the elbow joint is bent over or is positioned near the rest plate 28, and while the patient's lower arm or wrist is positioned in the wrist recess 84 on the wrist support attachment 70. Brace bracket 132 includes a rigid bar rigidly secured to or detachably securable to vertical extension 54 on base 50.

Referring again to FIG. 13, in some embodiments one or both arm braces are attached to arm brace bracket 132 at a pivoting brace joints 134a, 134b. For example, first arm brace 130a is attached to brace bracket 132 at a first pivoting brace joint 134a, and second arm brace 130b is attached to brace bracket 132 at a second pivoting brace joint 134b. In such embodiments, each arm brace can pivot to change orientation for accommodating different sized arms.

Figure 16A:
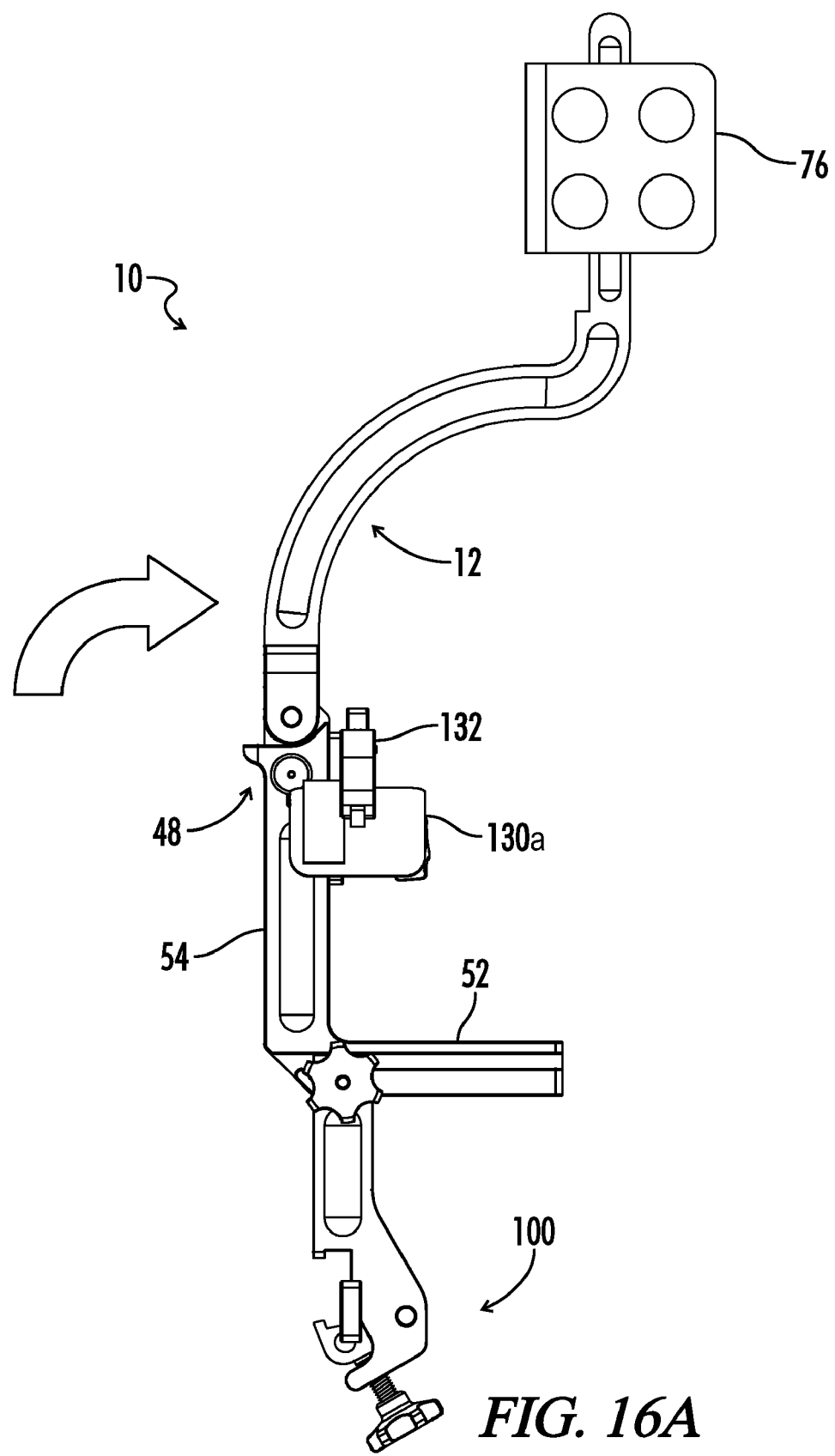
FIG. 16A illustrates a side elevation view of the embodiment of an arm stabilizer of FIG. 15 having a stabilizer bar in a vertical position.
Figure 16B:
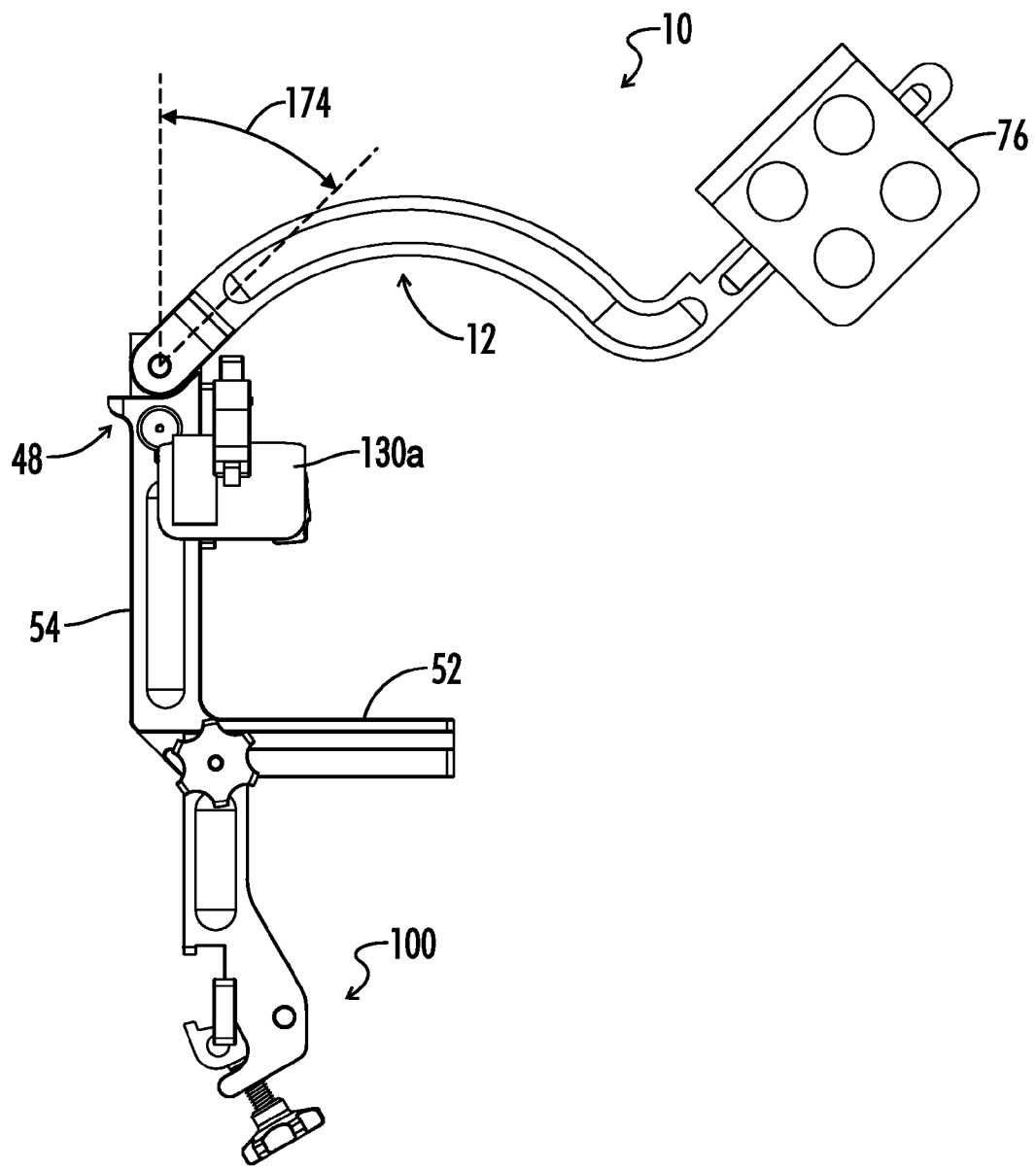
FIG. 16B illustrates a side elevation view of the embodiment of an arm stabilizer of FIG. 15 having a stabilizer arm in an extended position rotated away from the patient.
Figure 22:
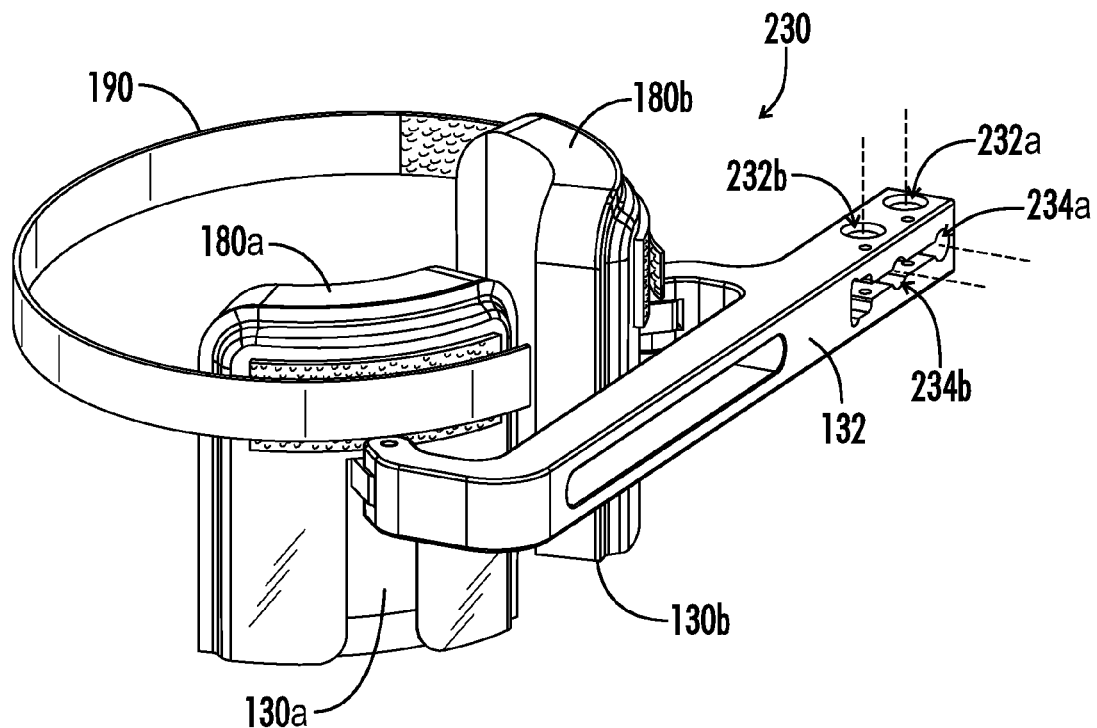
FIG. 22 illustrates a partial perspective view of an embodiment of a brace pad attachment including brace pads and brace strap attached in accordance with the present disclosure.

Also seen in FIG. 13, in some embodiments, arm brace attachment 230 is detachably securable to an arm brace stage 136. Arm brace bracket 132 includes a release switch 148 that can be manipulated to selectively remove arm brace bracket 132 from arm stabilizer 10. For example, as seen in FIG. 22, arm brace bracket 132 includes one or more primary bracket holes 234a, 234b having a first orientation. Primary bracket holes 234a, 234b engage corresponding stage posts 137a, 137b positioned on brace stage 136 for securing arm brace bracket 132 to arm brace stage 136. In some embodiments, arm brace bracket 132 includes secondary bracket holes 232a, 232b, having a second orientation substantially perpendicular to the first orientation of primary bracket holes 234a, 234b, for engagement with stage posts. When primary bracket holes 234a, 234b receive stage posts 137a, 137b, brace pad attachment 230 is positioned generally as seen in FIG. 13 such that the brace pads engage the tricep region of the upper arm. However, when secondary bracket holes 232a, 232b engage stage posts 137a, 137b, brace pad attachment 230 is positioned generally as seen in FIGS. 16A and 16B such that brace pads engage the bicep region of the upper arm. Each stage post 137a, 137b can include one or more stage post grooves 139a, 139b, respectively, for selectively engaging a corresponding structure release switch 148.

Figure 23A:
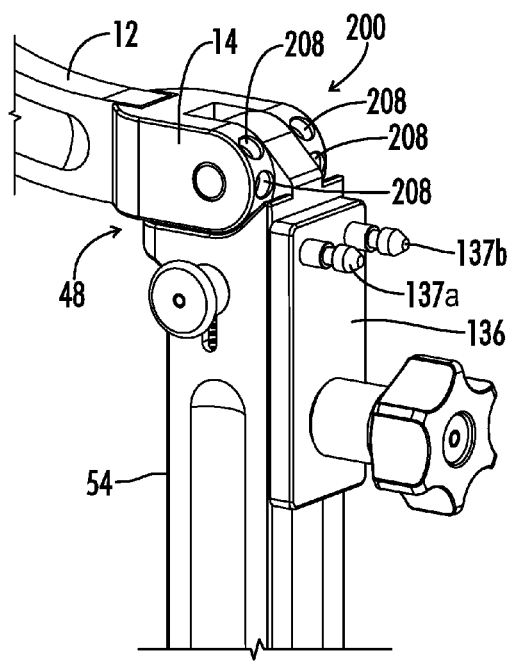
FIG. 23A illustrates a detail perspective view of an embodiment of a base hinge with a lock in accordance with the present disclosure.
Figure 23B:
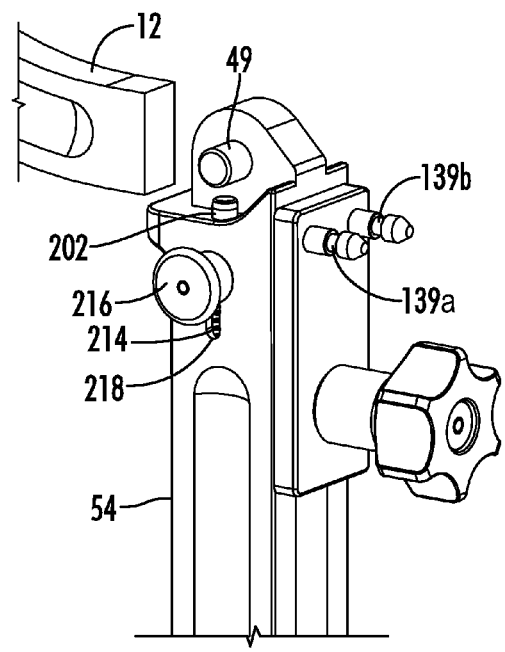
FIG. 23B illustrates a partial detail perspective view of an embodiment of a base hinge with a lock in accordance with the present disclosure.

Also seen in FIGS. 13, 23A and 23B, an arm brace stage fastener 138 is attached to arm brace stage 136. Arm brace stage fastener 138 engages a corresponding linear stage track 140 positioned on vertical extension 54 of base 50. An operator of arm stabilizer 10 can manually loosen arm brace fastener 138 and manually slide arm brace stage 136 up or down along stage track 140 to adjust the position of brace pad attachment 230, including first and second arm braces, relative to a patient's upper arm. When the desired position is reached, the operator can then manually re-tighten the arm brace stage fastener 138 to secure the brace pad attachment in position.

In some embodiments, each arm brace 130a, 130b includes a padded brace surface 142. In additional embodiments, each arm brace 130a, 130b is configured to receive a removable brace pad, or humerus pad.

Figure 21:
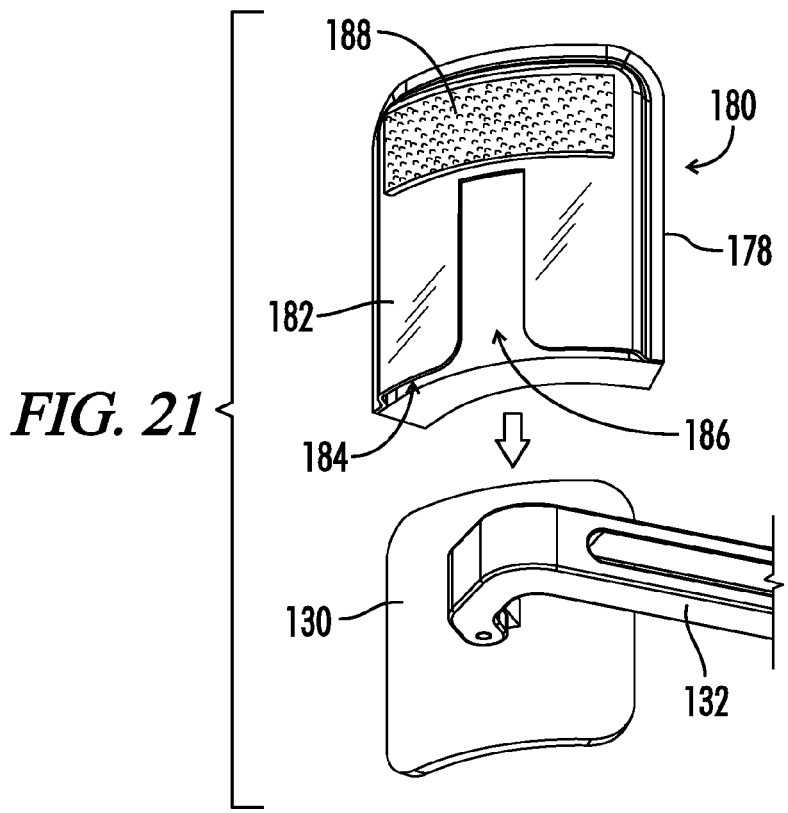
FIG. 21 illustrates a partial exploded perspective view of an embodiment of an arm brace and brace pad in accordance with the present disclosure.

In a further embodiment, the present invention provides a removable humerus pad 180, or brace pad, seen in FIG. 21, for attachment to an arm brace 130 on a device for stabilizing a human arm. The brace pad 180 includes a brace pad body 178 including a foam material, a gel material, a textile material, a padded material or another suitable material for engaging a patient's arm. A brace pad panel 182 is attached to the back of the brace pad body 178. The brace pad panel 182 defines a brace slot 184 between the brace pad panel 182 and the brace pad body 178. The brace slot 184 is generally shaped for receiving arm brace 130.

Each humerus pad 180 may be disposable in some embodiments. In some embodiments, the present invention provides a kit including a plurality of disposable humerus pads for attachment to an arm brace on an arm stabilizer.

Brace pads 180 are used to provide a padded contact between the patient's upper arm, i.e. humerus (bicep or tricep), and the arm stabilizer 10. Each brace pad 180 can include a disposable item in some embodiments. Prior to use, brace pad 180 can be slid onto arm brace 130 from above, as indicated by the arrow in FIG. 21. Brace slot 184 is generally dimensioned to slidably receive an arm brace 130, such as first or second arm brace 130a or 130b. In some embodiments, arm brace 180 is configured to be used interchangeably between first and second arm braces 130a, 130b. A bracket slot 186 is defined in brace pad panel 182. Bracket slot 186 is shaped to accommodate arm brace bracket 132, or another mounting structure on arm brace 130, when brace pad 180 is slid onto arm brace 130. One or more brace pad patches 188 can be positioned on each arm brace 180 in some embodiments. Each brace pad patch 188 can include a fastener such as a hook-and-loop type fastener material.

Referring now to FIG. 22, a brace pad strap 190 can be positioned on the arm stabilizer extending from first arm brace 130a to second arm brace 130b. A patient's upper arm can be secured to the arm stabilizer using brace pad strap 190. A first brace pad 180a is installed on first arm brace 130a, and a second brace pad 180b is installed on second arm brace 130b. Brace pad strap 190 extends from first brace pad 180a to second brace pad 180b, forming a loop. The patient's arm can be secured in the loop.

Referring again to FIG. 1, arm stabilizer 10 in some embodiments includes a base 50 pivotally attached to the stabilizer bar 12. A base 50 is pivotally attached to the stabilizer bar 12 at a base hinge 48. The base 50 includes a lateral rail 52 and a vertical extension 54 protruding generally upwards from the lateral rail 52. The base hinge 48 is formed between the proximal bar end 14 and the vertical extension 54. Base hinge 48 allows stabilizer bar 12 to be pivoted relative to base 50 as seen in FIGS. 16A and 16B. Stabilizer bar 12 can generally be pivoted away from a patient as seen in FIG. 16A. Such rotation of stabilizer bar 12 allows the patient's arm to be moved away from the patient. In the orientation seen in FIG. 16A, it is noted that arm brace attachment 230 can be repositioned such that first arm brace 130a and second arm brace 130b face generally toward lateral rail 52. As such, in this position, the user's bicep can be engaged by first and second arm braces 130a, 130b and the patient's lower arm and wrist can extend upward toward wrist support guide 76. Stabilizer bar 12 may be rotated about base hinge 48 into this position for a procedure or for rehabilitation or for another purpose such as taking a medical image of the patient's arm. For example, in some applications, it may be desirable for stabilizer bar 12 to be in a position such as that seen in FIG. 1, or the position seen in FIG. 16A, or any orientation therebetween. In a preferred embodiment, stabilizer bar 12 can also be secured at an intermediate angle between the position seen in FIG. 1 and the position seen in FIG. 16A. The intermediate angle includes about a forty-five degree angle in some embodiments.

As seen in FIG. 16B, in some embodiments, stabilizer bar 12 is pivotable about base hinge 48 away from the patient beyond the vertical orientation seen in FIG. 16A. In FIG. 16B, stabilizer bar 12 extends an extension angle 174 beyond vertical. In some embodiments, stabilizer bar 12 is pivotable to an extension angle up to about forty-five degrees or any angle in between vertical and the forty-five degree position seen in FIG. 16B. By providing a device having a stabilizer bar 12 pivotable away from the patient, the patient's arm can be extended away from the patient and the operating table for imaging of the arm without removing the arm from arm stabilizer 10. After the imaging is completed, the stabilizer bar 12 can be rotated about base hinge 48 back toward the patient for further operation, rehabilitation or rest.

Figure 23C:
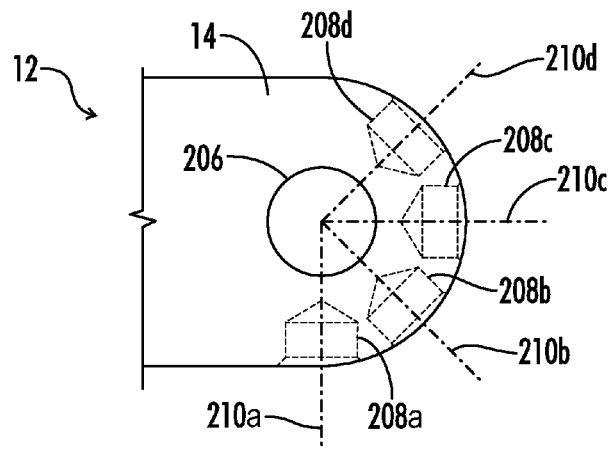
FIG. 23C illustrates a side elevation view of an embodiment of a proximal end of a stabilizer bar in accordance with the present disclosure.

Base hinge 48 includes a base hinge lock in some embodiments for securing stabilizer bar 12 at the desired angular orientation about base hinge 48 relative to base 50. Referring to FIGS. 23A, 23B and 23C, an embodiment of a base hinge lock 200 is generally illustrated. The base hinge lock 200 is operable to lock stabilizer bar 12 at a desired angular position relative to vertical extension 54 on the base. In one exemplary embodiment, base hinge lock 200 includes a plurality of lock holes 208 defined on proximal bar end 14 on stabilizer bar 12, seen in FIG. 23A. Each lock hole 208 is positioned to interchangeably engage a base hinge pin 202 protruding upward from vertical extension 54, as seen in FIG. 23B. Base hinge pin 202 is coupled to a pin spring 214 operable to resiliently bias base hinge pin 202 in the upward position, as seen in FIG. 23B. A lock knob 216 is mechanically linked to base hinge pin 202 through lock knob slot 218. Lock knob 216 can be translated downward through lock knob slot 218, thereby selectively moving, or releasing, base hinge pin 202 downward into a pin chamber and disengaging base hinge pin 202 from a corresponding lock hole 208 on proximal bar end 14. When lock knob 216 is positioned such that base hinge pin 202 is released, stabilizer bar 12 can be angularly pivoted about base hinge 48. In some embodiments, a hinge pin 49 forms an axis of rotation for pivoting stabilizer bar 12. The position of each pin socket 208 forms a predetermined angular location for stabilizer bar 12 in some embodiments. For example, as seen in FIG. 23C, a first pin socket 208a corresponds to a stabilizer bar position wherein proximal bar end 14 extends from vertical extension 54 at a substantially ninety degree angle, and first pin socket 208a is defined along a first socket axis 210a, as seen in FIG. 15. A second pin socket 208b is defined in proximal bar end 14 along a second socket axis 210b. In some embodiments, the angle between first and second socket axes is between about thirty and about sixty degrees. In other embodiments, the angle between first and second socket axes is about forty-five degrees. A third pin socket 210c is defined along a third socket axis 210c. In some embodiments, the angle between first socket axis 210a and third socket axis 210c is about ninety degrees. When base hinge pin 202 engages third pin socket 208c in some embodiments, stabilizer bar 12 is in the position seen in FIG. 16A. A fourth pin socket 208d is defined along a fourth socket axis 210d. In some embodiments, the angle between first and fourth pin socket axes is between about one-hundred-twenty and about one-hundred-fifty degrees. In a further embodiment, the angle between first and fourth pin socket axes is about one-hundred-thirty-five degrees. In some embodiments, when base hinge pin 202 engages fourth pin socket 208d, stabilizer bar 12 is in the position seen in FIG. 16B.

Referring to FIG. 13, an alternative embodiment of an arm stabilizer 10 is generally illustrated in a perspective view. Arm stabilizer 10 includes a rail clamp 100 secured to base 50. Rail clamp 100 includes a modular attachment that can be used to secure arm stabilizer 10 to a mounting structure 102. Mounting structure 102 could include any suitable structure for mounting arm stabilizer 10, such as a surgical table or bench or a patient's bed or chair. Rail clamp 100 can include various embodiments, seen in FIGS. 13, 14A and 14B. Rail clamp 100 includes a mounting recess 106 shaped to receive mounting structure 102. Mounting recess 106 is defined between a clamp body 120 and a pawl 110. Pawl 110 is pivotally attached to clamp body 120. Pawl 110 includes a pawl flange 112, seen in FIG. 14A, and clamp body 120 includes a body flange 122. Pawl flange 112 and body flange 122 protrude toward each other across mounting recess 106. Mounting structure 102 can be received in mounting recess 106, and pawl 110 can be pivoted toward mounting structure 102 using rail clamp fastener 104. In some embodiments, rail clamp fastener 104 includes a threaded screw or bolt inserted through a hole in the rail clamp. When rail clamp fastener 104 is screwed toward pawl 110, or tightened against clamp body, rail clamp fastener 104 engages pawl 110 and pushes pawl 110 toward mounting recess 106 and mounting structure 102. In some embodiments, pawl 110 is angularly moveable about a pawl pivot axis 124, seen in FIG. 14B. A pawl spring 126 can be positioned between pawl 110 and clamp body 120 for biasing pawl 110 toward rail clamp fastener 104. As such, when rail clamp fastener 104 is unscrewed away from pawl 110, pawl spring 126 maintains engagement between rail clamp fastener 104 and pawl 10, thereby allowing mounting structure 102 to be released from mounting recess 106.

Figure 14A:
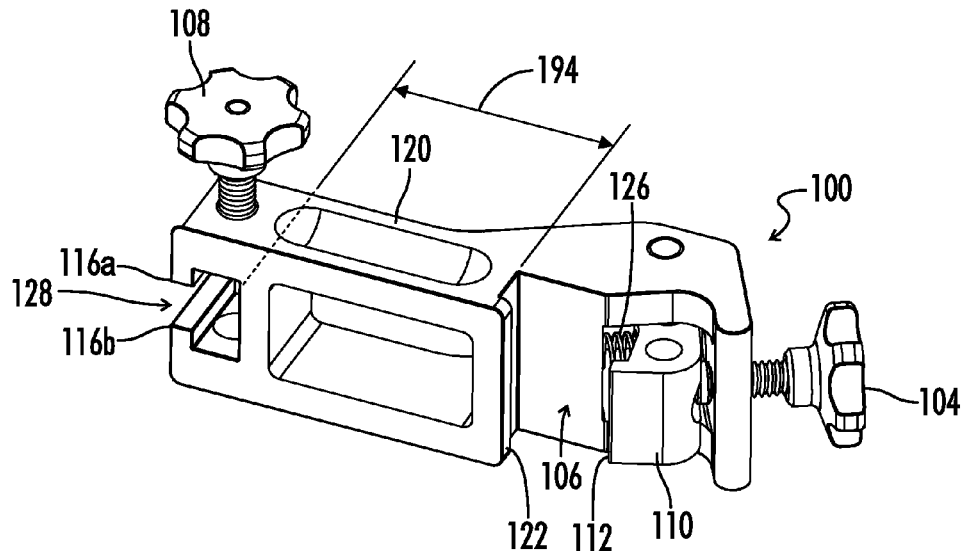
FIG. 14A illustrates a perspective view of an embodiment of a rail clamp in accordance with the present disclosure.
Figure 14B:
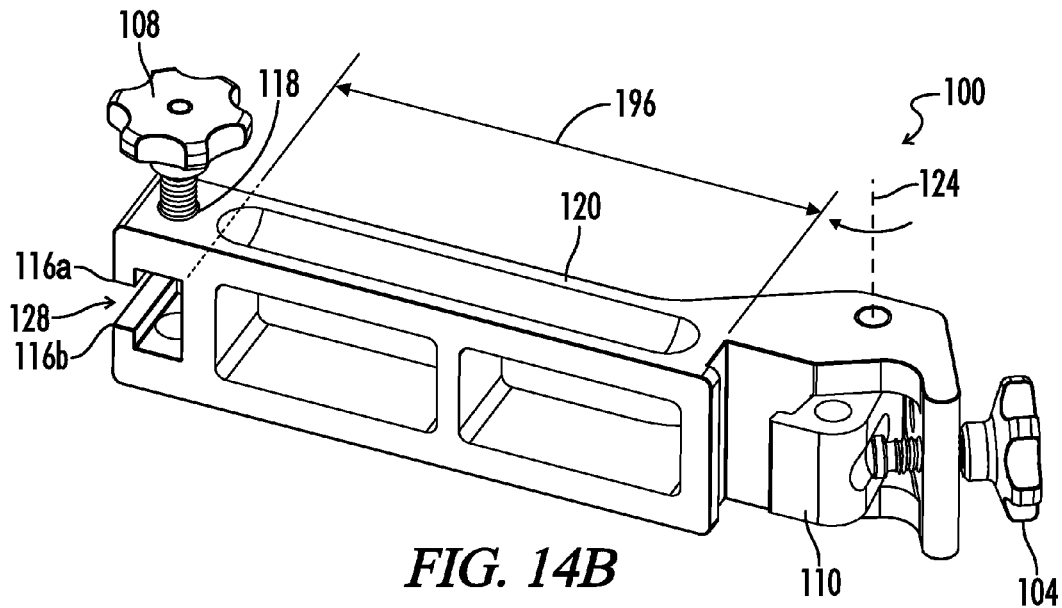
FIG. 14B illustrates a perspective view of an alternative embodiment of a rail clamp in accordance with the present disclosure.

Also seen in FIGS. 13, 14A and 14B, rail clamp 100 includes a rail gap 128 formed at the end of rail clamp 100 opposite pawl 110. Rail gap 128 can be formed in clamp body 120 in some embodiments. A first rail flange 116a and a second rail flange 116b protrude from clamp body toward rail gap 128. Each rail flange provides a retaining structure for engaging lateral rail 52 on base 50 of arm stabilizer 10. In some embodiments, lateral rail 52 on base 50 includes first and second rail grooves 56a, 56b. First rail flange 116a slidably engages first rail groove 56a, and second rail flange 116b slidably engages second rail groove 56b. A lateral rail fastener 108 is attached to rail clamp 100 and can be used to tighten rail clamp 100 against lateral rail 52.

Different rail clamps can include different lengths. For example, the rail clamp illustrated in FIG. 14A generally includes a first rail clamp length 194, and the rail clamp illustrated in FIG. 14B generally includes a second rail clamp length 196 greater than the first rail clamp length 194. Generally, a longer rail clamp is more effective for use with an arm stabilizer when used with a taller patient. For example, the rail clamp illustrated in FIG. 14A could be used more effectively with a person less than about six feet tall, and the rail clamp illustrated in FIG. 14B, having a greater length, could be used more effectively with a person greater than about six feet tall. In some embodiments, the present invention provides an arm stabilizer kit including a stabilizer bar, a first rail clamp having a first length and a second rail clamp having a second length, wherein the first length is less than the second length. As such, the kit provides multiple rail clamps for accommodating patients of differing heights.

It is noted that, in some embodiments, any one or more of the modular components for attachment to stabilizer bar 12 may be disposable. For example, in some embodiments, wrist support block 80 is a disposable part that may be thrown away after use. In a further embodiment, wrist support attachment 70 may be a disposable part. Additionally, one or more parts of reducer attachment 20 can be disposable. Each disposable part in some embodiments includes a plastic material.

Thus, although there have been described particular embodiments of the present invention of a new and useful Arm Stabilizer Device and Methods, it is not intended that such references be construed as limitations upon the scope of this invention except as set forth in the following claims.

What is claimed is:

1. An arm stabilizer apparatus for clamping to a mounting structure, comprising:
   a stabilizer bar having a distal bar end and a proximal bar end;
   a reducer attachment detachably secured to the stabilizer bar between the distal bar end and the proximal bar end;
   a wrist support attachment detachably secured to the stabilizer bar between the reducer attachment and the distal bar end, the wrist support attachment including a guide bar slidably disposed on the stabilizer bar and a wrist support guide attached to the stabilizer bar; and
   a base pivotally attached to the stabilizer bar at a base hinge, the base including a lateral rail and a vertical extension protruding generally upwards from the lateral rail, the base hinge being formed between the proximal bar end and the vertical extension.

2. The apparatus of claim 1, further comprising:
   a rail clamp including a clamp body securable to the lateral rail, the rail clamp including a rail flange operable to releasably engage the lateral rail.

3. The apparatus of claim 2, further comprising:
   the rail clamp including a mounting recess shaped for receiving the mounting structure;
   a pawl pivotally attached to the rail clamp extending into the mounting recess, the pawl being angularly moveable toward the mounting structure; and
   a rail clamp fastener attached to the rail clamp, the rail clamp fastener operable to move the pawl toward the mounting structure.

4. The apparatus of claim 3, further comprising:
   a pawl spring disposed between the clamp body and the pawl.

* * * * *